United States Patent [19]
Kutner et al.

[11] Patent Number: 5,387,404
[45] Date of Patent: * Feb. 7, 1995

[54] PROCESS AND APPARATUS FOR HEAT DISINFECTING SOFT CONTACT LENSES

[75] Inventors: Barry S. Kutner, Wilton; Daniel A. Latowicki, Newtown, both of Conn.; Kenneth E. Malech, Briarcliff Manor, N.Y.

[73] Assignee: Flexiclave, Inc., Briarcliff Manor, N.Y.

[*] Notice: The portion of the term of this patent subsequent to Aug. 13, 2008 has been disclaimed.

[21] Appl. No.: 16,581

[22] Filed: Feb. 10, 1993

Related U.S. Application Data

[63] Continuation-in-part of Ser. No. 835,309, Feb. 14, 1992, Pat. No. 5,248,478, which is a continuation-in-part of Ser. No. 692,736, Apr. 29, 1991, which is a continuation-in-part of Ser. No. 184,246, Apr. 21, 1988, Pat. No. 5,019,344.

[51] Int. Cl.$^6$ ............................................. A61L 2/12
[52] U.S. Cl. ........................... 422/299; 422/288; 422/294; 422/298; 422/305; 219/687; 219/729; 250/455.11; 134/901
[58] Field of Search ............... 422/21, 28, 294, 305, 422/298, 299, 307, 288; 219/10.55 F, 10.55 M, 10.55 E; 250/455.1; 206/5.1; 134/901, 105, 102.1

[56] References Cited

U.S. PATENT DOCUMENTS

| | | | |
|---|---|---|---|
| 3,801,278 | 4/1974 | Wagner et al. | 422/307 |
| 4,582,076 | 4/1986 | Prat | 422/307 |
| 4,826,658 | 5/1989 | Kay | 422/28 |
| 4,851,631 | 7/1989 | Wendt | 219/10.55 F |
| 4,880,951 | 11/1989 | Levinson | 219/10.55 F |
| 4,894,503 | 1/1990 | Wendt | 219/10.55 F |
| 4,926,020 | 5/1990 | Atwell et al. | 219/10.55 F |
| 4,971,773 | 11/1990 | Rohrer et al. | 422/21 |
| 5,039,495 | 8/1991 | Kutner et al. | 422/299 |

*Primary Examiner*—Robert J. Warden
*Assistant Examiner*—Hien Tran
*Attorney, Agent, or Firm*—Steinberg, Raskin & Davidson

[57] ABSTRACT

Apparatus for disinfecting soft contact lenses includes a vessel at least partially formed of material transparent to microwave electromagnetic radiation, disinfecting solution receivable within the vessel, a device for irradiating the disinfecting solution within the vessel with microwave electromagnetic radiation, and shielding apparatus for defining a radiation shielded interior portion within the vessel receivable of contact lenses and disinfecting solution, and an unshielded interior portion within the vessel which is in fluid communication with the shielded portion.

16 Claims, 8 Drawing Sheets

PROCESS AND APPARATUS FOR HEAT DISINFECTING SOFT CONTACT LENSES

This is a continuation-in-part of application Ser. No. 07/835,309 filed Feb. 14, 1992 now U.S. Pat. No. 5,248,478, which is a continuation-in-part of application Ser. No. 07/692,736 filed Apr. 29, 1991, which is a continuation-in-part of application Ser. No. 07/184,246, filed Apr. 21, 1988, now U.S. Pat. No. 5,019,344.

BACKGROUND OF THE INVENTION

This invention relates generally to processes and apparatus for disinfecting soft contact lenses and, more particularly, to processes and apparatus for disinfecting soft contact lenses by heat disinfection.

In caring for hydrophilic gel (soft) contact lenses, attention must be directed toward, among other things, maintaining lens hydration and protecting the lenses from pathogens. Exposure of soft contact lenses to heat or to the action of soaking solutions are the techniques used to provide the disinfection necessary to protect soft contact lenses from pathogens.

Disinfecting lenses by soaking in germicidal solutions is a two step process which includes soaking the lenses in the solution until the lens is disinfected, and then rinsing the lenses with a rinsing solution prior to insertion. Typically, lenses are stored in a germicidal solution, such as one that derives its germicidal activity from thimerosal or chlorhexidine, for at least four hours and then are rinsed in a saline solution. Such techniques are time consuming, require the user to keep different solutions on hand, and risk eye irritation should the disinfecting solution not be adequately rinsed from the lenses.

For heat disinfection, it is generally necessary to heat soft contact lenses to a temperature of 80° C. for at least 10 minutes. To insure lens hydration, the gel lenses are immersed in saline solution in their storage case which is then placed within a boiling unit. Although gel lenses can be disinfected in a shorter time by heat than by soaking, conventional heat disinfection techniques require a separate heating unit which adds to the expense of lens care. Moreover, in practice, heat disinfection of lenses is a relatively time-consuming procedure which necessitates that the wearer use an alternate pair of lenses, or eyeglasses, while disinfection proceeds.

SUMMARY OF THE INVENTION

It is an object of the present invention to provide new and improved processes and apparatus for disinfecting soft contact lenses.

Another object of the present invention is to provide new and improved processes and apparatus for disinfecting soft contact lenses by heat.

Still another object of the present invention is to provide new and improved processes and apparatus for the heat disinfection of soft contact lenses in a rapid manner.

A further object of the present invention is to provide new and improved processes and apparatus for disinfecting soft contact lenses by heat using a heating source commonly found in many households thereby eliminating the need to purchase a separate heating unit.

Briefly, in accordance with the present invention, these and other objects are attained by a process in which a disinfecting solution is introduced into a vessel that is at least partially formed of material transparent to microwave electromagnetic radiation, and introducing the soft contact lenses into an interior portion of the vessel that is substantially shielded from microwave electromagnetic radiation, either before or after the disinfecting solution has been introduced, such that the contact lenses are placed into contact with the disinfecting solution. The vessel is closed and then subjected to microwave electromagnetic radiation to heat the disinfecting solution with which the lenses are in contact, while the lenses themselves are shielded from the radiation. Irradiation continues until the lenses are disinfected.

The vessel preferably comprises a collapsible pouch formed of flexible, vapor-impermeable sheet material which expands to a visibly apparent distended condition during the irradiating step to provide a visual indication that disinfection is proceeding.

The irradiating step is preferably accomplished by placing the closed vessel containing the radiation-shielded lenses and disinfecting solution within the cavity of a conventional microwave oven of the type found in many households.

According to one embodiment of the invention, the shielded interior portion of the vessel is provided by lens holder apparatus which comprise shielding means that define compartments that are receivable of the contact lenses. The lens-receiving compartments are in fluid communication with the surrounding interior of the vessel to permit the lenses to be in contact with the disinfecting solution while irradiation continues. In another embodiment of the invention, shielding means are integrated with the vessel, such as by providing shielding material on portions of the vessel wall, to define a shielded interior portion of the vessel.

DESCRIPTION OF THE DRAWINGS

A more complete appreciation of the present invention and many of the attendant advantages thereof will be readily understood by reference to the following detailed description when considered in connection with the accompanying drawings in which:

FIGS. 3a–3d are views of the lens holder apparatus of FIG. 2 for providing a radiation-shielded interior portion of the pouch of FIG. 2 wherein FIG. 3a is a top plan view of the holder apparatus when open, FIG. 3b is a bottom plan view thereof, FIG. 3c is a top plan view of the holder apparatus when closed, and FIG. 3d is a section view taken along line d—d of FIG. 3c;

DESCRIPTION OF THE PREFERRED EMBODIMENTS

Figure 1:
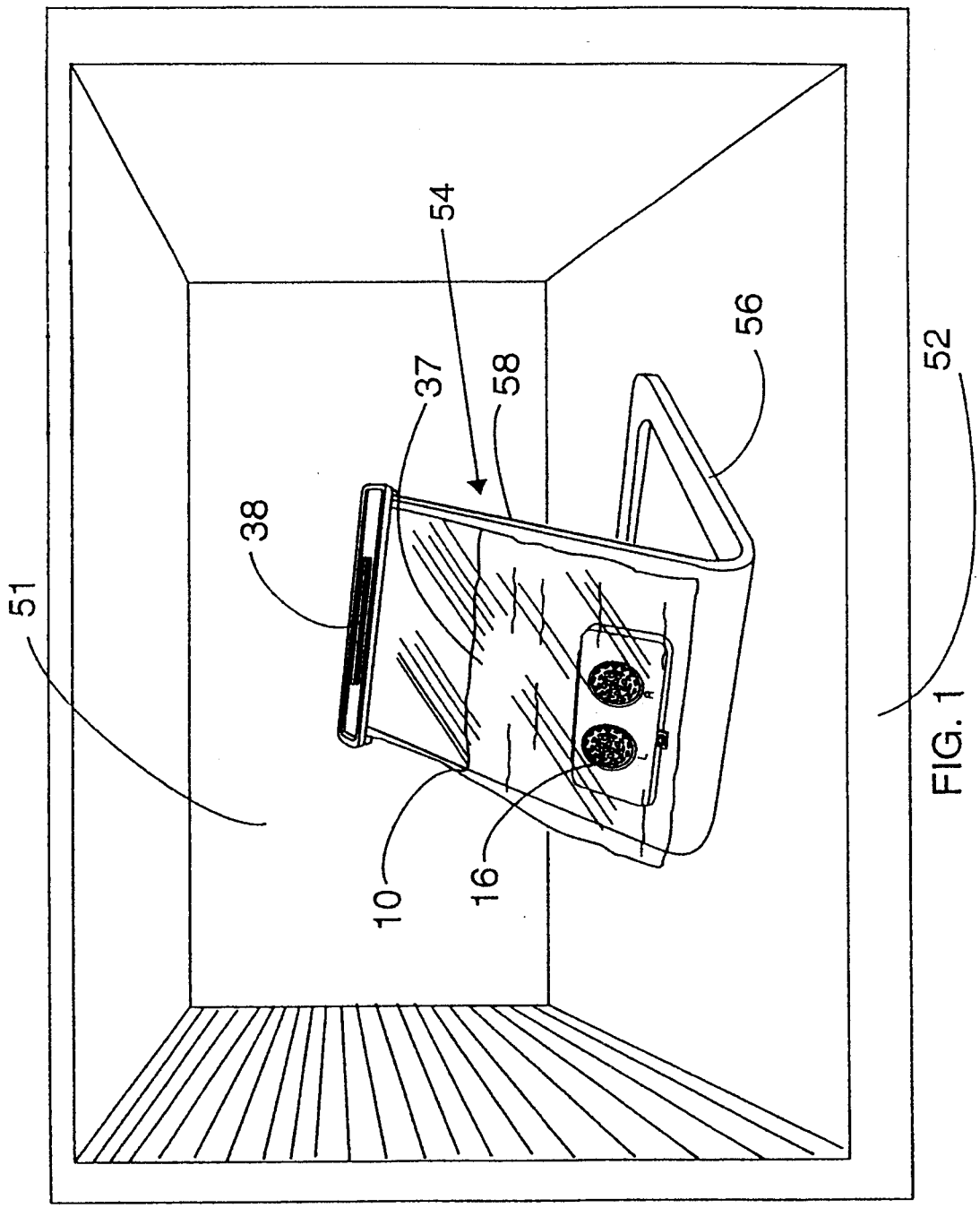
FIG. 1 is an orthogonal view of apparatus for disinfecting soft contact lenses in accordance with one embodiment of the invention.
Figure 2:
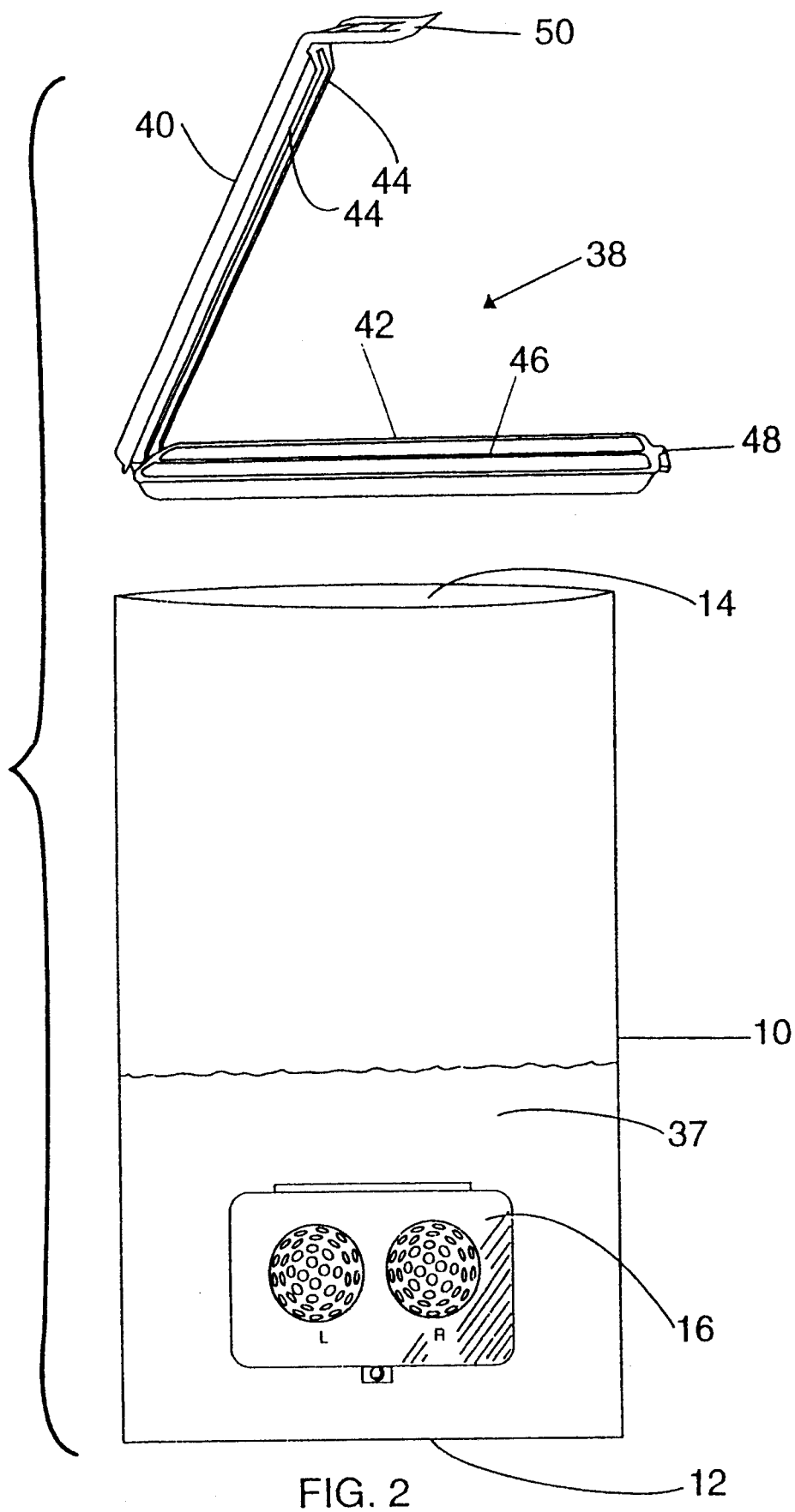
FIG. 2 is an elevation view of an assembly of a pouch, lens holder apparatus and disinfecting solution, including a clamp for sealing the pouch, in accordance with the embodiment of the invention shown in FIG. 1.

Referring now to the drawings wherein like reference characters designate identical or corresponding parts throughout the several views, and more particularly to FIGS. 1-3, apparatus for disinfecting soft contact lenses in accordance with one embodiment of the invention comprises an assembly including a pouch 10 formed of material transparent to microwave electromagnetic radiation which contains a disinfecting solution 37, contact lens-receiving holder apparatus 16 which provides an interior portion of the pouch which is in fluid communication with the remainder of the pouch interior, but which is shielded from microwave radiation, and a clamp 38 for closing the pouch. The closed pouch assembly is supported on a fixture 54 within the cavity 51 of a conventional microwave oven 52 of the type commonly found in many households, as described below.

The pouch 10 (FIG. 2) is formed of flexible sheet material comprising a laminate of polypropylene and polyester transparent to microwave electromagnetic radiation. The pouch 10 may be constructed from a tubular web of such sheet material having a sealed end 12 and an open end or mouth 14.

Figure 3A:
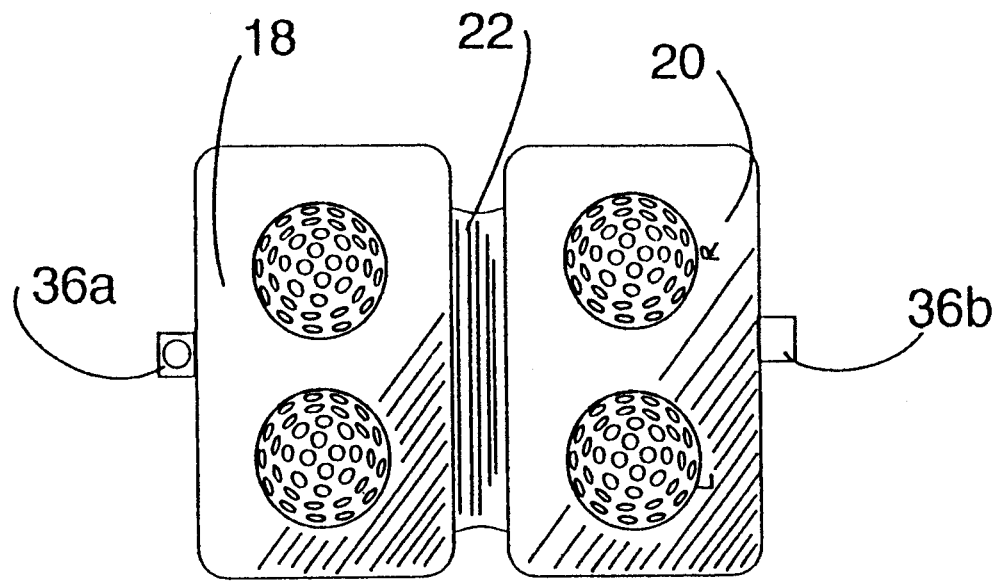
Figure 3B:
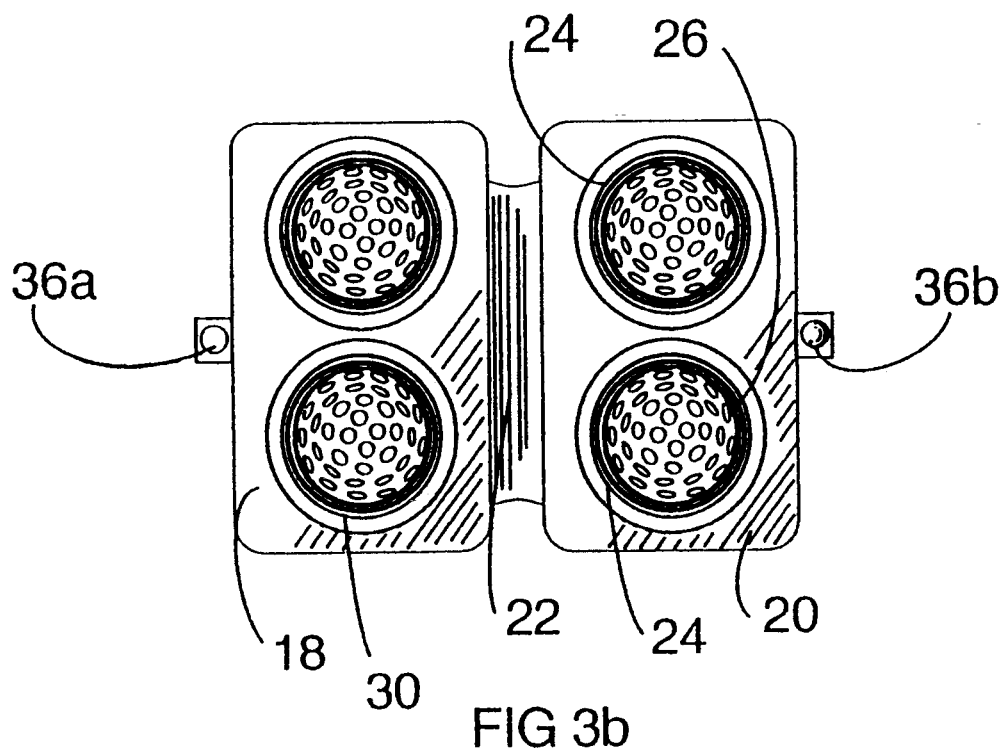
Figure 3C:
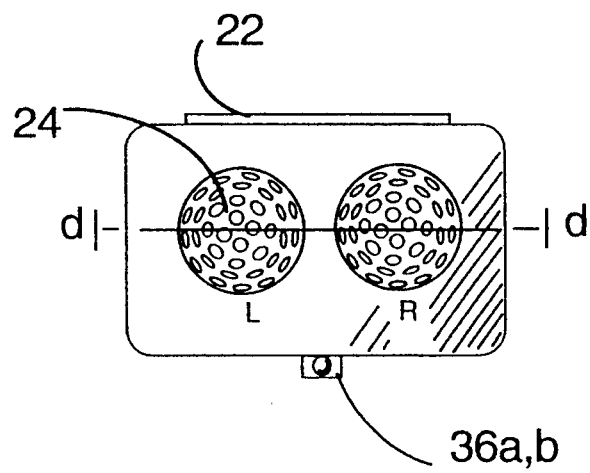
Figure 3D:
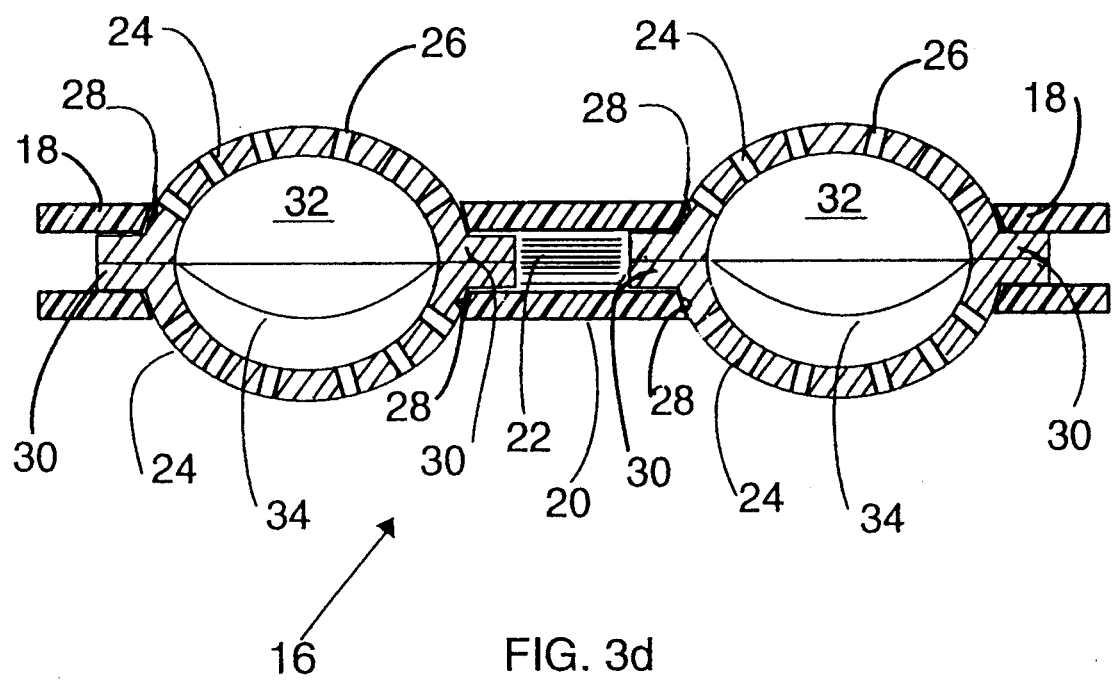

Referring to FIGS. 3a-3d, the lens holder apparatus 16 comprises a pair of planar cover members 18, 20 formed of polypropylene connected to each other by an integral hinge portion 22. A pair of circular openings 28 (FIG. 3d) are formed in corresponding locations in each of the cover members 18, 20 in which substantially dome-shaped members formed of stainless steel material 24 are affixed and through which small apertures or perforations 26 are formed. The dome-shaped members are preferably coated with Teflon material to promote removal of the contact lenses from the holder apparatus during use. Each dome-shaped member 24 has a peripheral rim 30 which engages and is affixed to the peripheral region of a respective opening 28 on the inside surface of a respective cover member 18, 20 so that the dome-shaped portion of member 24 extends through the opening 28 and protrudes beyond the outer surface of the cover member. As seen in FIGS. 3c and 3d, upon folding the cover members 18 and 20 onto each other, about hinge portion 22, each dome-shaped member 24 affixed to cover member 18 moves into contiguous relationship with a corresponding dome-shaped member 24 affixed to the other cover member 20, with the peripheral rims 30 of the pairs of contiguous dome-shaped members 24 of cover members 18 and 20 abutting against each other to thereby define a pair of compartments 32 for receiving a pair of contact lenses 34. The interior of the compartments 32 are shielded from exposure to microwave radiation by the metallic material of the dome-shaped members. The apertures 26 formed in the sheet material of the dome-shaped members provide fluid communication between the interiors of compartments 32 and the remainder of the pouch interior. However, the apertures 26 are sufficiently small that microwave electromagnetic radiation is prevented from passing into the interior of the compartments 32. An opening in a clip or locking member 36a connected to cover member 18 is adapted to receive a projection on a locking member 36b connected to cover member 20 when the holder apparatus is closed to secure the holder apparatus in its closed position.

Figure 4A:
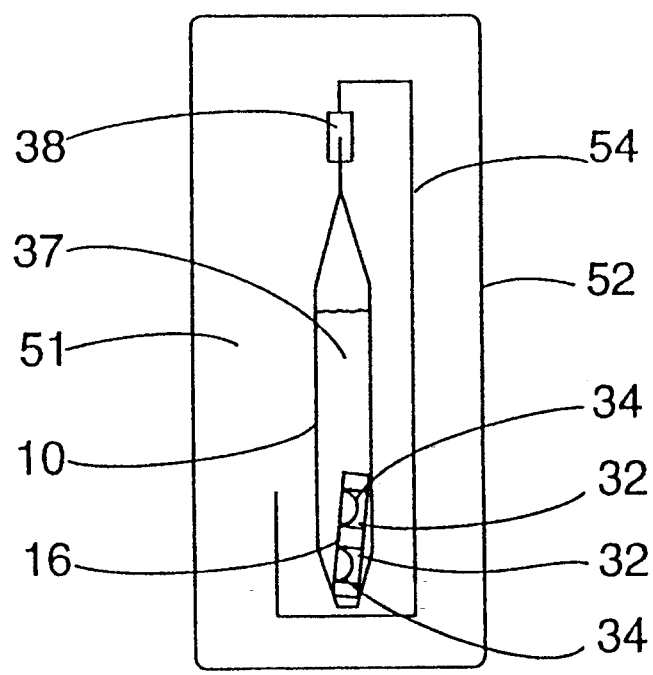
FIGS. 4a and 4b are schematic illustrations depicting a process in accordance with the invention.
Figure 4B:
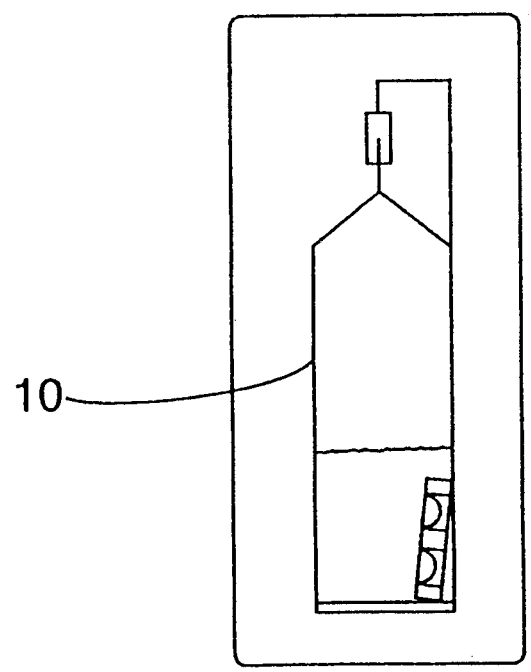

Referring to FIGS. 1 and 4, in the operation of the apparatus in accordance with the process of the invention, the contact lenses 34 are situated in the shielded compartments 32 of the holder apparatus 16 by placing each of them into the concave depression of a respective one of the pair of dome-shaped members 24 of one of the cover members 18, 20, and then closing the holder apparatus as described above whereupon the lenses become situated in respective shielded compartments 32. The clips 36a, 36b are applied to lock the holder apparatus.

The holder apparatus 16 containing the contact lenses 34 is introduced into the pouch 10 through its open end or mouth 14. Saline solution 37 is introduced into the pouch so that the holder apparatus 16 is completely immersed in the solution. For example, the saline solution may be introduced using an aerosol dispenser or from a unit dose ampule. Since the apertures 26 provide fluid communication between the interior of the contact lens-receiving compartments 32 and the surrounding pouch interior, the saline solution fills the compartments 32 and contacts the lenses 34. The mouth 14 of pouch 10 is then sealed by means of clamp 38 (FIG. 2) so that the pouch is substantially liquid-tight, but such that vapor generated during the disinfecting process will be vented from the pouch when a threshold internal pressure is exceeded. The clamp 38 is formed of plastic and includes a pair of legs 40, 42 pivotally connected to each other at one of their ends. A pair of longitudinal ribs 44 are formed on leg 40 while a single rib 46 is formed on the other leg 42, positioned to snugly interfit between ribs 44 when legs 40, 42 are closed. When the legs 40, 42 are thus clamped over the mouth 14 of pouch 10, the plastic sheet material of the pouch is tightly corrugated by the ribs 44, 46 to form a liquid-tight seal. A locking protrusion 48 and cooperating latch 50 are provided on the free ends of legs 40 and 42 to lock the clamp 38 to the mouth 14 of pouch 10.

The thus-formed sealed assembly comprising the pouch 10, the saline solution 37 and contact lens-containing holder apparatus 16, is then mounted on the fixture 54 (FIG. 1) and situated in the cavity 51 of the microwave oven 52. Fixture 54 comprises a base 56 from which a planar supporting wall 58 extends upwardly at an angle to the horizontal. The sealed assembly is supported on wall 58 by fastening clamp 38 to its top by any suitable means, such as by Velcro fasteners.

Irradiation of the assembly with microwave electromagnetic radiation then proceeds whereupon the saline disinfectant solution is substantially immediately heated under the thermal effects of the microwave radiation while the contact lenses 34 are shielded from the radiation within compartments 32 of holder apparatus 16. The heated disinfectant solution is in constant contact with the lenses and the lenses are disinfected by heat within a relatively short time. In this embodiment, the holder apparatus 16 thus constitutes shielding means for dividing the interior of the vessel or pouch 10 into a shielded interior portion, compartment 32, which is substantially free of microwave radiation during the irradiation process, and the remaining interior portion which is unshielded.

The embodiment of the invention described above is particularly advantageous insofar as a visual indication that disinfection is proceeding. In particular, as the sealed assembly is irradiated, the disinfectant solution 37 begins to vaporize. As the vapor pressure within pouch 10 increases, the pouch 10 expands to a distended condition, schematically depicted in FIG. 4b, to provide an easily recognizable visual indication that disinfection is proceeding. Vapor is vented from within the pouch when the internal pressure exceeds a certain threshold to eliminate any possibility of rupture of the pouch.

In one specific embodiment of the invention, the pouch 10 has a volume of about 50 cc, and is filled with about 20 cc of saline solution. The sealed assembly is irradiated with microwave electromagnetic radiation at a power of about 700 watts for about 30 seconds. Under these conditions, the temperature of the saline solution is increased to 100° C. in several seconds, and disinfection of the contact lenses is completed in about 30 seconds. In accordance with the invention, the volume of disinfectant solution is generally in a range of between about 10 to 40 cc, while the assembly is irradiated with radiation at a power in the range of between about 500 to 1000 watts for a time in the range of between about 15 to 60 seconds. The pouch clamp 38, fixture 54 and cover members of the lens holder apparatus are preferably formed of polypropylene and the dome-shaped members 24 of the holder apparatus 16 are preferably formed of stainless steel.

Another advantage of the invention described above is that irradiation of the sealed assembly may continue until the disinfecting solution 37 itself is substantially disinfected. The pouch 10 is maintained in a sealed condition after completion of the irradiating step with the lenses in contact with the disinfectant solution. In this manner, the lenses are protected from recontamination until future use.

Figure 5:
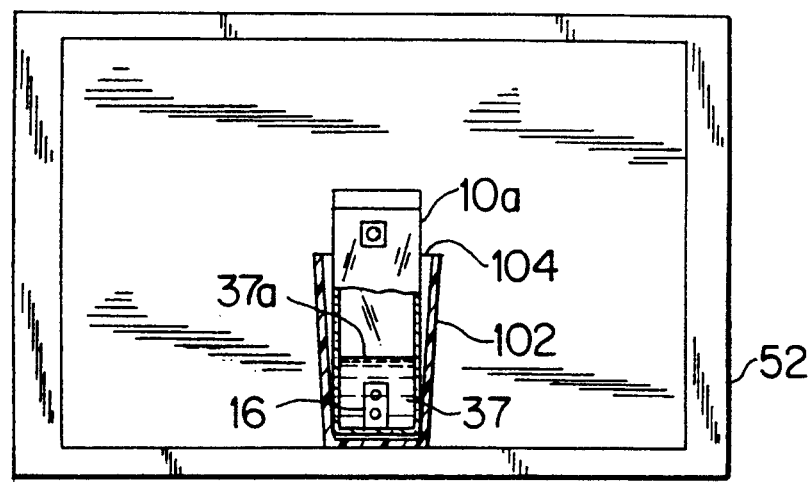
FIG. 5 is a front elevation view in partial section of apparatus for disinfecting soft contact lenses in accordance with another embodiment of the invention.
Figure 6:
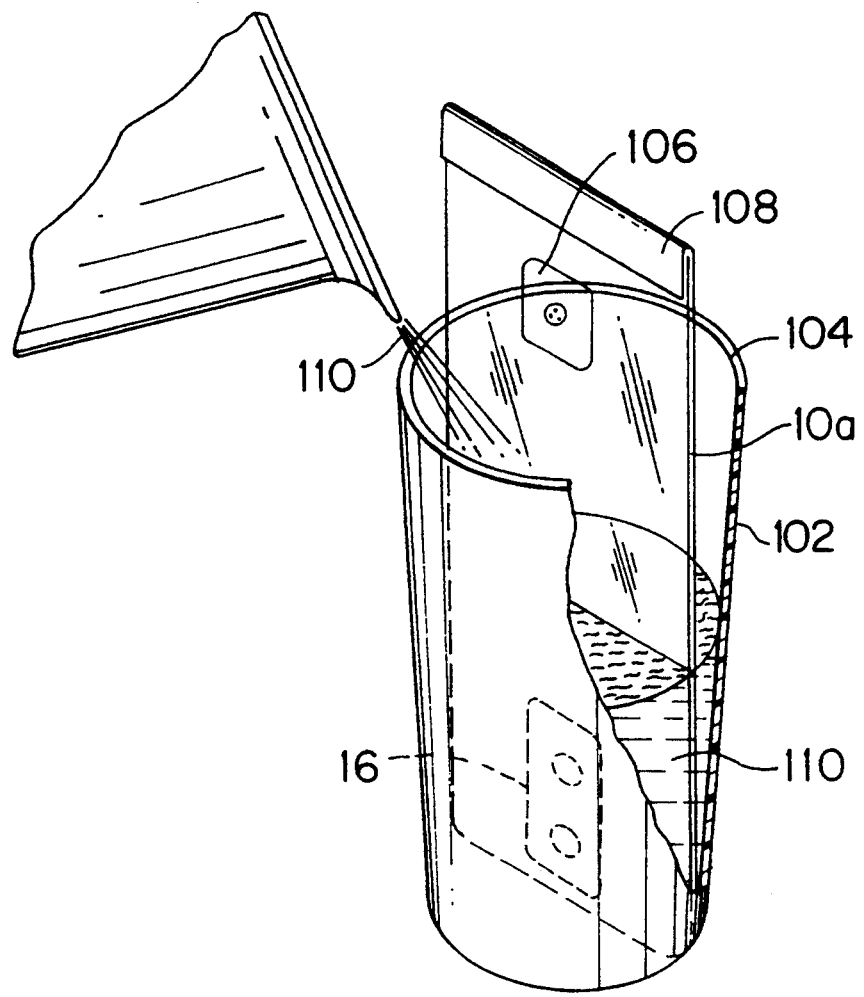
FIG. 6 is a perspective view, partially broken away, of an assembly of a pouch, lens holder apparatus, disinfection solution and cup-shaped holder member after disinfection and illustrating a step of cooling the disinfecting solution.

The invention is not restricted to the particular components described above. Referring to FIGS. 5 and 6, an arrangement in accordance with the invention is shown in which an assembly comprising a pouch 10a containing the saline solution 37 and contact lens-containing holder apparatus 16 is situated in microwave oven 52 and held during irradiation by means of a cup-shaped holder member 102 instead of by means of the fixture 54 of FIGS. 1 and 4. In particular, cup-shaped holder member 102 is formed of polypropylene or other suitable microwave transparent material and has an interior configuration shaped so that the pouch 10a containing the solution 37 and the lens-containing holder apparatus 16 can be inserted and held in a substantially vertical orientation with minimum distortion of the pouch while allowing for expansion of the pouch upon irradiation. In the illustrated embodiment, the inner diameter of the cup-shaped member 102 is substantially equal to the width of the pouch 10 in its unexpanded state so that the sides of the pouch substantially engage the wall of the cup-shaped holder member which thus holds the pouch in a substantially vertical orientation. The height of cup-shaped holder member 102 is such that the lip 104 is situated above the level 37a of solution 37 for reasons discussed below. In lieu of using the venting clamp 38, a wall of the pouch 10a incorporates a one-way vapor vent 106 of the type available from PyMaH Corporation of Somerville, N.J. The mouth of the pouch is sealed at 108, such as by heat sealing or by means of a suitable adhesive.

The disinfecting process proceeds in a manner similar to that described above. The holder member 102 holding the pouch 10a containing solution 37 and lens-containing holder apparatus 16 is situated in the cavity of a microwave oven 52 whereupon the assembly is irradiated with microwave radiation to heat the saline solution while the contact lenses are shielded within holder apparatus 16. The heated disinfecting solution is in contact with the lenses which are disinfected by heat in a short time.

The use of a cup-shaped holding member 102 in lieu of a fixture 54 or the like provides important advantages. For example, vertical orientation of the pouch 10a allows the lens-containing holder apparatus 16 to be completely immersed in a lesser amount of saline solution than is required in the case where the pouch is oriented at an angle as seen in FIG. 1. In the event that a leak develops in the pouch 10a, the saline solution 37 will be captured and retained in the cup-shaped holder apparatus.

Moreover, after the disinfection procedure has been completed, the assembly can be easily removed from the microwave oven by grasping the holder member 102 without danger of touching the hot pouch. As seen in FIG. 6, the holder member 16 may then be filled with cold tap water 110 in order to accelerate cooling of the hot saline solution by conduction through the pouch wall. Since the pouch is not permeable, the tap water will not come into contact with the disinfected contents of the pouch but functions only as means for cooling the contents of the pouch. In this manner the pouch may be drained without danger of scalding and the lenses cooled so that they may be safely inserted in the eye only 30-45 seconds after the disinfection procedure has been completed.

Figure 7:
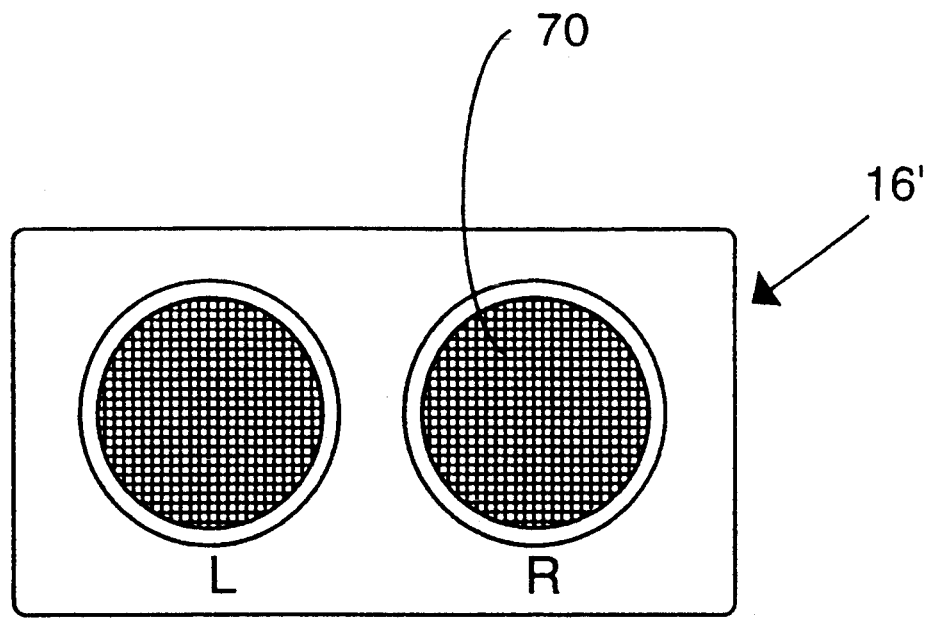
FIG. 7 is a top plan view of an alternate embodiment of lens holder apparatus for providing a shielded interior portion of a vessel for receiving contact lenses to be disinfected.

Lens holder apparatus may be used in which the shielded lens-receiving compartments are formed of different shielding material than that from which the compartments 32 of lens holder apparatus 16 are formed. For example, referring to FIG. 7, lens-receiving compartments 70 of holder apparatus 16' may be defined by a double-layered knitted mesh of tin-copper-steel wire of the type available from the Tecknit Company of Cranford, N.J. under the designation EMC Shielding Tape. The knitted wire mesh provides fluid communication between the interior of the lens-receiving compartments, yet provides effective shielding against the passage of microwave electromagnetic radiation.

Other disinfecting solutions than saline solution may be utilized. For example, a 3% solution of hydrogen peroxide or an isotonic solution containing boric acid may be utilized. In principle, the process and apparatus of the invention need not be limited to the use of a flexible pouch, and any suitable vessel may be utilized.

Figure 8:
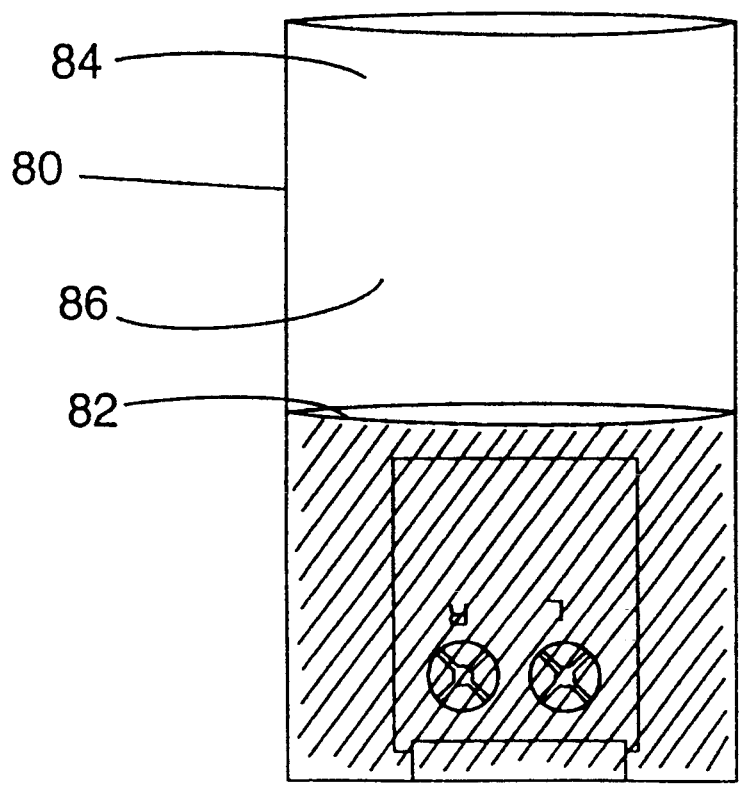
FIG. 8 is a view similar to FIG. 2 of an assembly of a pouch, lens holder apparatus and disinfecting solution, according to another embodiment of the invention.

The interior portion of the pouch which is shielded from microwave radiation may be defined by means other than the lens holder apparatus. For example, referring to FIGS. 8 and 9, a pouch 80 may be utilized formed of flexible plastic material over a surface portion of which a metallic coating 82 is deposited. Thus, the pouch 80 includes an upper part (as seen in FIG. 8) 84 which is formed of material transparent to microwave electromagnetic radiation and a lower part 86 which is formed of material that is opaque to microwave electromagnetic radiation, i.e., plastic sheet material provided with a metallic coating. The metallic coating 82 thus surrounds an interior portion of the pouch which is thereby shielded from microwave radiation.

Figure 9:
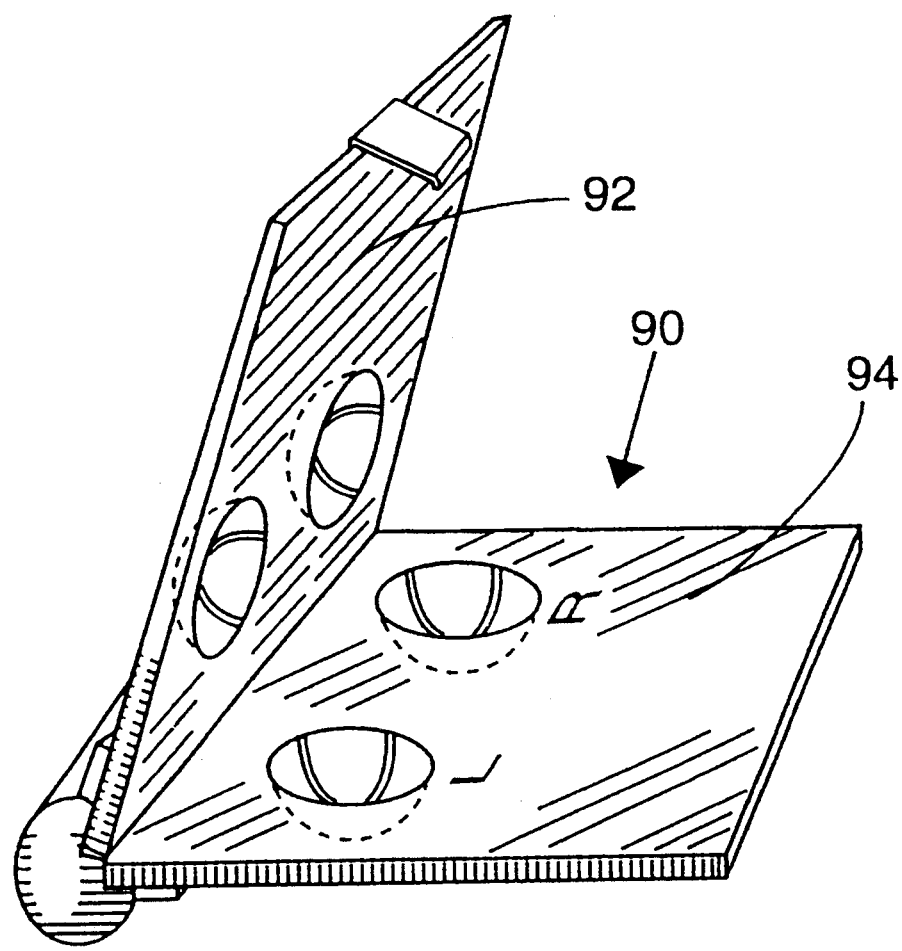
FIG. 9 is a perspective view of lens holder apparatus used in the embodiment of the invention illustrated in FIG. 8.

The contact lenses to be disinfected are situated in the shielded interior portion of pouch 80 by means of holder apparatus 90 shown in FIG. 9. Such holder apparatus is substantially conventional and is essentially defined by a pair of pivotally connected cover members 92, 94 having respective pairs of openings over which concave plastic gratings are provided to define compartments for receiving the respective contact lenses.

In use, the lenses are placed in the respective compartments of the holder apparatus 90 which is then placed in the shielded interior portion of pouch 80. Disinfecting solution is introduced into the pouch to immerse the holder apparatus and lenses. Sufficient disinfectant solution is provided so that at least a portion is situated in the unshielded interior portion of the pouch so that when the sealed assembly is exposed to microwave radiation, the disinfecting solution is heated while the lens are shielded, to thereby disinfect the lenses. Thus, in this embodiment, the metallic coating 82 provided over the lower part 86 of pouch 80 constitutes shielding means integrated with the pouch or vessel 80 for dividing the interior of the vessel 80 into a shielded interior portion and an unshielded interior portion in fluid communication with the shielded portion which is exposed to microwave radiation during irradiation.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. An apparatus for heat disinfecting soft contact lenses, comprising:
   a vessel having an interior, said vessel being at least partially formed of material transparent to microwave electromagnetic radiation;
   disinfecting solution receivable within said vessel;
   means for irradiating said disinfecting solution within said vessel with microwave electromagnetic radiation; and
   shielding means for dividing the interior of said vessel into at least one shielded interior portion which is substantially free of microwave electromagnetic radiation during irradiation of said disinfecting solution within said vessel by said irradiating means, and an unshielded interior portion in fluid communication with said shielded portion and which is exposed to said microwave electromagnetic radiation during irradiation of said vessel by said irradiating means, said shielded interior portion being receivable of contact lenses.

2. The apparatus as recited in claim 1 wherein said vessel comprises a collapsible pouch formed of flexible, vapor-impermeable sheet material transparent to microwave radiation.

3. The apparatus as recited in claim 2 wherein said sheet material of which said pouch is formed comprises a laminate of flexible polypropylene and polyester.

4. The apparatus as recited in claim 1 wherein said vessel is substantially closed and comprises means for at least partially venting vaporized disinfecting solution from within said vessel.

5. The apparatus as recited in claim 1 wherein said shielding means comprises means for holding the contact lenses in said at least one shielded interior portion in contact with said disinfecting solution.

6. The apparatus as recited in claim 1 wherein said shielding means comprises a compartment for the contact lenses, said compartment being formed by perforated sheet metal material.

7. The apparatus as recited in claim 1 wherein said vessel is at least partially formed of material opaque to microwave electromagnetic radiation to thereby constitute said shielding means such that said shielding means are integrated with said vessel.

8. The apparatus as recited in claim 1 wherein said disinfecting solution comprises saline solution.

9. The apparatus as recited in claim 1 wherein said disinfecting solution comprises hydrogen peroxide.

10. An apparatus for heat disinfecting soft contact lenses, comprising:
    shielding means for substantially surrounding contact lenses for shielding the lenses from microwave electromagnetic radiation;
    a pouch formed of flexible vapor-impermeable sheet material transparent to microwave electromagnetic radiation, said pouch having means defining an opening through which the contact lenses and disinfecting solution are introduced into said pouch, said opening being closable after introduction of the contact lenses and said disinfecting solution to form a liquid-tight assembly;
    disinfecting solution being contained within said pouch in a quantity sufficient to remain in contact with said contact lenses;
    means for irradiating said liquid-tight assembly with microwave electromagnetic radiation to heat said disinfecting solution with the lenses introduced in said pouch remaining in contact with said heated solution and with said shielding means providing a barrier to prevent transmission of substantial microwave electromagnetic radiation onto the lenses, whereby the contact lenses are heat disinfected.

11. The apparatus as recited in claim 10, wherein said shielding means are arranged in an interior of said pouch to define a shielded interior portion of said pouch, said shielding means comprising a holder member receivable of the contact lenses.

12. The apparatus as recited in claim 11 wherein said holder member includes a receptacle for retaining the contact lenses, said receptacle having wall means defining an interior, and wherein said shielding means further includes microwave electromagnetic radiation shield material surrounding said interior of said receptacle.

13. The apparatus as recited in claim 12 wherein said microwave electromagnetic radiation shield material comprises metallic wire-mesh material.

14. The apparatus as recited in claim 10 wherein a portion of said pouch is formed of material opaque to microwave electromagnetic radiation to thereby constitute said shielding means such that said shielding means and said pouch comprise an integrated unit.

15. The apparatus as recited in claim 14 wherein said opaque material is a metallic coating provided on said portion of said pouch which is thereby shielded from microwave electromagnetic radiation.

16. The apparatus as recited in claim 10, further comprising:
    a cup-shaped holding means formed of microwave-transparent material for holding said liquid-tight pouch assembly during irradiation.

* * * * *